United States Patent [19]

Ford

[11] Patent Number: 5,720,728
[45] Date of Patent: Feb. 24, 1998

[54] TEARDROP SHAPED PRESSURIZING APPARATUS

[75] Inventor: Dixon A. Ford, Farmington, Utah

[73] Assignee: Mallinckrodt Medical, Inc., St. Louis, Mo.

[21] Appl. No.: 621,973

[22] Filed: Mar. 25, 1996

[51] Int. Cl.⁶ .................................................. A61H 5/00
[52] U.S. Cl. ........................ 604/131; 604/132; 604/141
[58] Field of Search ................................ 604/131, 132, 604/133, 140, 141, 142, 143, 144, 146; 128/DIG. 12

[56] References Cited

U.S. PATENT DOCUMENTS

| | | | |
|---|---|---|---|
| 817,054 | 4/1906 | Gay | 604/141 |
| 4,673,392 | 6/1987 | Keime | 604/141 |
| 4,735,613 | 4/1988 | Bellin et al. | 604/141 |
| 4,828,546 | 5/1989 | McNeil et al. | 604/133 X |
| 5,106,374 | 4/1992 | Apperson et al. | 128/DIG. 12 X |
| 5,181,910 | 1/1993 | Scanlon | 128/DIG. 12 X |
| 5,242,406 | 9/1993 | Gross et al. | 604/132 |
| 5,342,313 | 8/1994 | Campbell et al. | 604/132 X |
| 5,368,569 | 11/1994 | Sanese | 604/141 X |
| 5,496,303 | 3/1996 | Antonetti | 604/144 X |

*Primary Examiner*—Sam Rimell
*Attorney, Agent, or Firm*—Madson & Metcalf

[57] ABSTRACT

A pressurizing apparatus for pressurizing fluid contained in a patient fluid bag is described which has a novel teardrop pressurizing chamber. The pressure apparatus includes a door and base which each have complimentary teardrop cavities formed therein. When the door is in the closed position over the base, the teardrop pressurizing chamber is formed. A teardrop bladder bag is located interior to the base and can be inflated to apply pressure to a patient fluid bag. A regulator allows adjustment of the desired pressure. A gauge allows monitoring of the pressure. A valve allows the pressurizing device to be turned on and off. The teardrop pressurizing chamber allows the pressurizing apparatus to come up to pressure in a more expeditious manner. The conformance of the pressurizing means to the teardrop pressurizing chamber also adds to the efficiency of the pressurizing of the patient fluid bag and, additionally, allows for uniform pressure throughout a procedure.

18 Claims, 7 Drawing Sheets

TEARDROP SHAPED PRESSURIZING APPARATUS

BACKGROUND OF THE INVENTION

1. The Field of the Invention

This invention relates to medical pumps generally and, more specifically, to an apparatus for pressurizing fluids contained in a fluid bag.

2. Background Art

Various medical procedures utilize devices which apply pressure to fluid bags. For example, intravenous delivery of blood, blood components, volume expanders or other parenteral fluids is often accomplished using an infusion pump to provide pressurized delivery. One method of accomplishing this pressurized delivery is to apply pressure to a fluid bag. Pressure for such systems is provided by hand pumping or by automatic pressurizing systems which utilize a continuous pressure source, such as compressed air.

As another example, fluids used for irrigation during surgery are often required to be pressurized. In some surgical irrigation systems, gravity is used to produce the fluid flow. Gravity produces a weak stream of fluid at the operative site, however, and pressurizing systems, designed to produce a higher pressure stream, have been developed. Among the first to be developed were systems using hand pumps. Surgical irrigation typically requires higher pressures than would be used for intravenous infusion of parenteral fluids. A significant effort is therefore required for hand pumping.

Often, the same basic pressurizing system is used to obtain a pressurized fluid bag in these various applications, although systems used for irrigation typically have some modifications to accommodate the higher pressures.

Such a pressurizing system will typically include a pressurizing chamber which will accommodate a fluid bag, a pressure inlet, a pressurizing device, a regulator, a gauge and a valve. The pressure inlet connects to the pressure source to provide pressure. The pressurizing device applies pressure to the fluid bag as it hangs in the pressurizing chamber. The regulator allows for setting and adjusting the desired pressure. The gauge allows for monitoring the pressure. Finally, the valve allows the system to be turned on and off.

In a common pressurizing system the fluid bag is placed within a pressurizing chamber. The pressurizing chamber is formed from complimentary rectangular cavities formed in the base and the door. When the door is closed over the base, the cavities come together to form a chamber. Typically, the base and door are not flush against each other. Rather there is a gap. The fluid bag extends slightly into this gap from the force of gravity. When pressure is applied to the fluid bag, it may extend slightly further into the gap. A typical pressurizing system utilizes a pressurizing means to apply pressure to the fluid bag. A common pressurizing means is an air inflated bladder bag.

When using such a pressurizing system, the fluid bag is typically hung on a hang tab and a hinged door is shut and fastened over the fluid bag securing it within the base. The base and the door having complimentary cavities formed therein which, together, form the pressurizing chamber. The base and the door typically have a hinge connecting one edge and some method of holding the door shut on the other edge. The base has the bladder bag assembled into it in such a way that the bladder bag, when inflated, applies pressure to the fluid bag. The bladder bag has a connection for a pressure source and a connection for vent. The bladder bag is connected to a hand pump, a small air compressor or other pressure source. The pressurizing system would have a valve with an "on" position and an "off" position, a regulator to allow for adjustment of the pressure to be maintained, and a gauge for monitoring the pressure. The pressure source inflates the bladder bag, to the pressure which has been selected, when the valve is placed in the on position. The bladder bag applies pressure to the fluid bag resulting in pressurized delivery of the fluid contained therein.

When the bladder bag is inflated and it applies pressure to the fluid bag it also has the affect of applying pressure to the door. This pressure on the door forces the door out slightly against a latch. The latch keeps the door from opening and results in the door being held firmly in place. In order to open the door the toggle switch of the valve must be placed in the "off" position. When in the "off" position the valve allows the pressure in the bladder bag to be released through a vent. This takes the pressure off of the fluid bag which, in turn, takes the pressure from the door. The door can then be moved inward, the latch undone, and the door opened. This procedure can be followed at the completion of use of the apparatus to remove the fluid bag. This procedure would also be followed during use of the apparatus when it is necessary to replace a depleted fluid bag with a new fluid bag.

Such systems typically will maintain a preset pressure. The desired pressure is set by adjusting the regulator and can be monitored on the gauge. These pumps typically will automatically maintain a preset pressure.

When used in infusion applications, the fluid bag will be connected to intravenous apparatus. In irrigation applications, the fluid bag will be attached to irrigation apparatus. Other applications requiring pressurization of a fluid bag can also use such apparatus.

Typically, the pressurizing chamber is of a generally rectangular shape of substantially equal cross section throughout. The fluid bag is also of a generally rectangular shape and, when lying on a horizontal surface, of a substantially equal cross section throughout. When the fluid bag is hung vertically inside the pressurizing chamber, however, the force of gravity causes the fluid bag to assume a teardrop or pendulous shape. Thus the shape of the pressurizing chamber and the shape of the fluid bag do not conform to each other when in use.

The non-conformity between the pressurizing chamber and the fluid bag has several disadvantages. For example, the difference in contour results in relatively large void at the top of the bag. Also there is a substantial amount of dead space at the top of the pressurizing system. This extra space results in a longer period of time for the system to come up to the set pressure and be ready for use after the fluid bag is mounted within the pressurizing chamber. This time delay, though relatively small, can be significant when occurring during a surgical procedure. When a surgeon is anxious to get started or to proceed and must wait for the equipment, any time delay can be disturbing. A larger air compressor may be utilized to cut down the pressurizing time but this results in higher cost and larger, more expensive equipment.

As another example of the disadvantages of having a non-conforming pressurizing chamber, the difference in contour causes the fluid bag to tend to bulge out between the base and the door impeding the closing of the door. Typically, the pressurizing chamber is designed to be approximately the size of the fluid bag when the fluid bag is lying on a horizontal surface. When the fluid bag is hung in a vertical position, the force of gravity pulls the fluid to the bottom of the bag and the bag bulges out some what. In order to close the door the user must manipulate the bag so that it recedes into the base. Failure to properly manipulate the bag can result in the fluid bag being pinched between the door and the base. The need to manipulate the bag to close the door adds to the time delay when initially setting up a fluid bag for infusion or irrigation and when changing a fluid bag. Again, although the time delay may seem fairly minimal to an outside observer, it is substantial to those involved in performing the procedure.

Manipulating the bag to fit within a non-conforming pressurizing chamber essentially involves pushing the column of fluid up, against the force of gravity. This can require a great deal of force, particularly when dealing with larger fluid bags. In the case of 1 liter and larger bags, the force required may be so great that some users are unable to close the door of the pressurizing chamber.

Alternatively, if the pressurizing chamber is formed so that you can place the bag inside and have the door close easily, the additional space decreasing the effectiveness of the pressurizing device. In this situation, because the pressurizing chamber is still generally rectangular with an equal cross section throughout, the addition of space on the bottom would also add extra space at the top of the chamber. This extra space would have to be overcome by the pressurizing apparatus inflating the bladder. Such additional space in the pressurizing chamber adds to the time it takes for the system to come up to pressure and the capability of pressure source required to adequately reach and maintain the pressure in a reasonable time.

The non-conformity between the pressurizing chamber and the fluid bag may also result in waste of the fluid. A non-conforming pressurizing chamber may not allow for an even application of pressure to the fluid bag, thus some amount of fluid may remain in the fluid bag. Depending on the fluid being used, the expense of this unusable fluid may be significant, particularly over the course of numerous procedures.

Additionally, forcing the fluid column up to allow closure of the door causes a certain mount of pressure to be placed On the fluid bag prior to the exertion of any pressure by a pressurizing device. This initial pressurization is inherent in non-conforming pressurizing chamber systems. An artifact of such initial pressurization is that the pressure reading on a monitoring gauge will not accurately reflect the actual pressure of the fluid leaving the fluid bag. Typically monitoring gauges monitor the inlet pressure. If there were no initial pressurization, the inlet pressure would accurately reflect the actual pressure of the fluid out of the fluid bag.

The non-conformity between the fluid bag and pressurizing chamber can also result in some pressure differential during the course of a procedure and the associated use of fluid from the fluid bag. The initial pressurization in such a system can cause the pressure of fluid flowing from the bag to be higher initially. The non-conformities between the fluid bag and pressurizing chamber may also cause non-uniform application of pressure to the fluid bag and result in pressure variations, of fluid flowing from the fluid bag, over the course of the procedure.

An additional problem arises from the construction of the hinges which attach the door to the base. The hinges are typically of a two piece construction, commonly fashioned from plastic. The pumps are cleaned between uses and the plastic hinges can be weakened by the application of cleaning solutions. The weakened hinges have been known to blow off in the midst of a surgical procedure. As is easily imagined, such an event is quite startling, particularly in the midst of a delicate surgical procedure. Such an event can even result in inadvertent harm to the patient. At the least, the temporary lack of fluids for infusion or irrigation can be quite serious.

Both the problems associated with the variance between the contour of the pressurizing chamber and the contour of a hanging fluid bag and the problems associated with the hinges used in such applications are common to pressure systems in the art and have not been adequately addressed by previous advancements.

BRIEF SUMMARY AND PRINCIPAL OBJECTS
OF THE INVENTION

The present invention is an apparatus for pressurizing fluids to be infused or fluids to be used for irrigation. The pressurizing apparatus comprises a pressurizing chamber having a pendulous shape of substantially the same contour as a fluid filled bag has when hanging in a vertical position. The pressurizing chamber comprises a base, a door, and an apparatus for applying pressure. The base and door each have a cavity formed therein such that, when the door is closed and secured in place, a pressurizing chamber having a pendulous shape is formed.

In a preferred embodiment, the base has a bladder bag, for applying pressure to the fluid bag, installed therein as well as a regulator, valve, gauge, and associated tubing. The valve is a three way valve which allows the bladder bag to be inflated when switched to the on position, or deflated when switched to the off position. The regulator is used to set the desired pressure. The gauge allows monitoring of the pressure. The tubing is attached to a pressure source such as the oxygen, air, or nitrogen outlets common to medical facilities. Inflation of the bladder bag pressurizes the fluid bag by applying pressure to it.

The door of the pressurizing chamber is preferably fabricated of a transparent material to allow for unrestricted viewing of the fluid level in the fluid bag. The door can be made of other materials, however, a means for viewing the fluid level is desirable.

The door and the base are joined to each other preferably be means of a hinge on one edge and a latch on the other. The latch fits around a lip formed in the door and the pressure applied to the fluid bag forces the door, and thus the lip, out slightly keeping the latch securely engaged with the door.

Accordingly, it is a primary object of the present invention to provide a pressurizing chamber of a shape to lessen the unutilized space between a patient fluid bag and the pressurizing chamber when the bag is hung and secured within the pressurizing chamber.

A further object of the invention is to provide a pressurizing chamber of a shape to allow for ease in closure of the door of the pressurizing chamber when a fluid filled bag is contained therein.

Another object of the invention is to provide a bladder bag which conforms to the shape of the base when exhausted and the shape of the door when extended.

An additional object of the present invention is to provide a pressurizing apparatus which allows for consistent pressure exerted against the fluid bag through-out a procedure.

A related object of the invention is to provide an attachment means, for joining the base and the door, which is less susceptible to failure of the sort which results in the door to the pressurizing chamber blowing off when the fluid bag is under pressure.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention briefly described above will be rendered by reference to the presently understood best mode for making and using the same, as illustrated in the appended drawings. Understanding that these drawings depict only typical embodiments of the invention and are therefore not to be considered as limiting of its scope, the invention will be described with additional specificity and detail through use of the accompanying drawings in which.

DETAILED DESCRIPTION OF THE INVENTION

Figure 1:
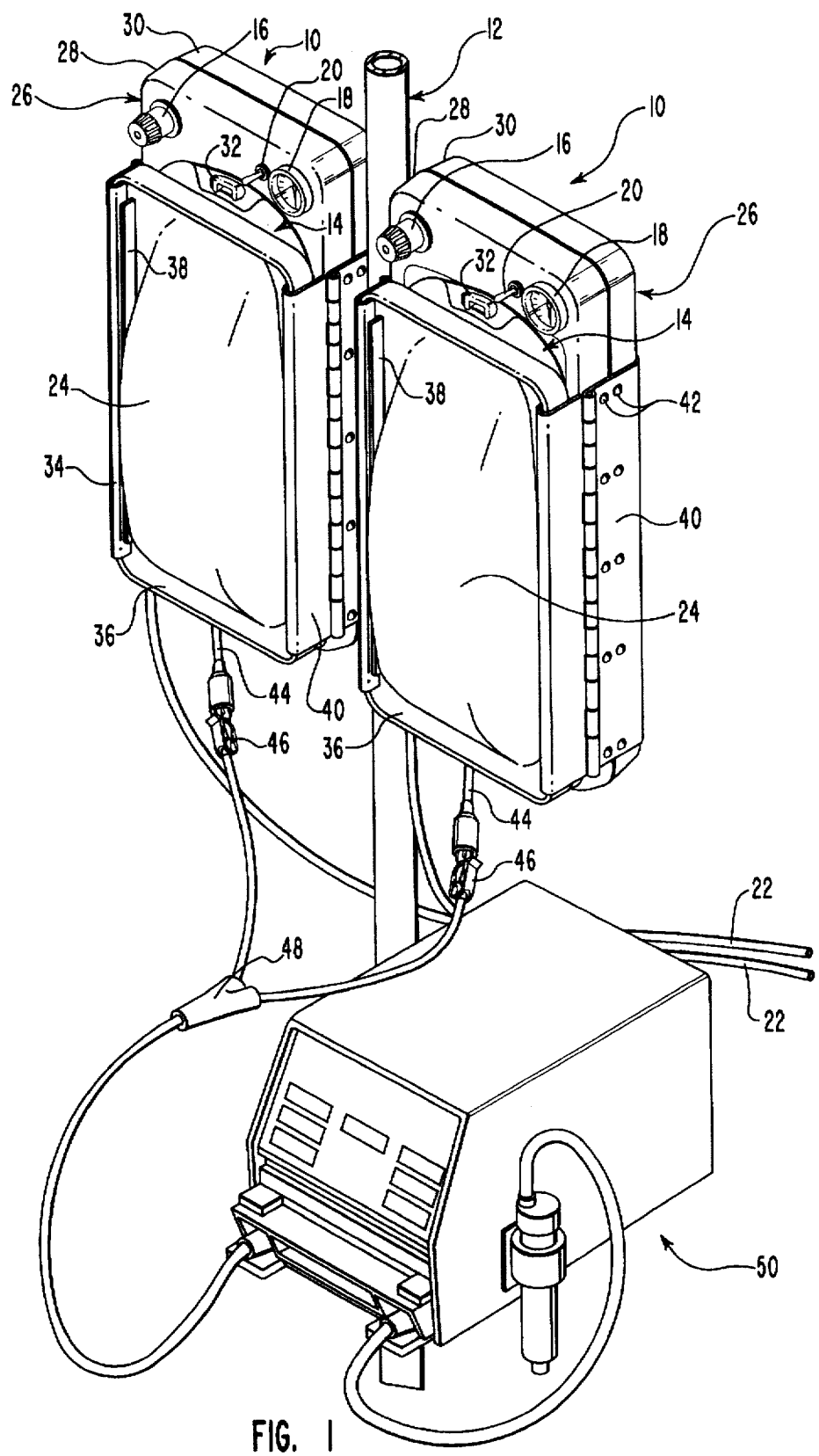
FIG. 1 is a perspective view showing a pair of the inventive pressurizing apparatus and associated equipment as they would be used in a typical medical environment application.

In this description, the term proximal is used to indicate the segment of the device normally closest to the operator when it is seen or being used. The term distal refers to the other end. Reference is now made to the embodiments illustrated in FIGS. 1–6 wherein like numerals are used to designate like parts throughout. A currently preferred embodiment of the inventive pressurizing apparatus is generally designated at 10 in FIG. 1. Each apparatus is mounted on I.V. pole 12 using a mounting brackets (not shown). A patient fluid bag 14 is enclosed within each pressurizing apparatus 10. A regulator 16 allows for setting and adjustment of pressure on each pressurizing apparatus 10. Pressure is monitored via a gauge 18. Valve 20 permits the system to be turned on and off. Valve 20 preferably includes a toggle switch which can be flipped up to the "on" position or down to the "off" position.

Pressure source tubing 22 is connected to a pressure source (not shown) such as oxygen, air or nitrogen outlets, a hand pump, or an electrical pump. Oxygen, air, or nitrogen outlets are commonly available in medical settings such as hospitals and clinics to provide a pressure source.

The pressurizing apparatus of the present invention also comprises a door 24 and a base assembly designated generally as 26. Door 24 is preferably constructed of clear polycarbonate material. Constructing door 24 of a clear material allows for easy viewing of the fluid level in patient fluid bag 14. It will be appreciated that any see through material of adequate strength to accommodate the pressures involved could be used. Additionally, it will be appreciated that opaque materials could also be used but some means for monitoring the fluid level in the patient fluid bag would be required.

Figure 2:
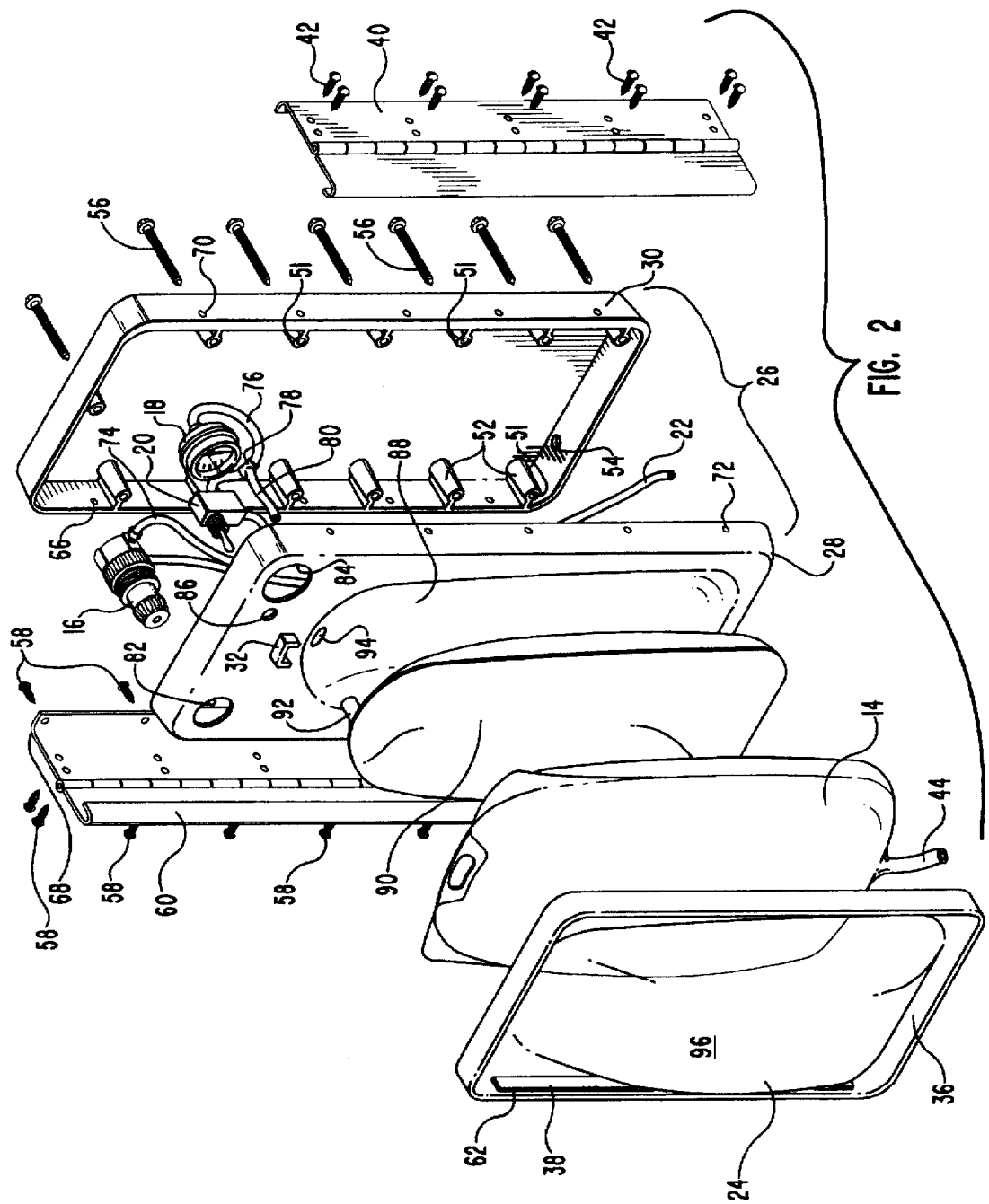
FIG. 2 is an exploded perspective view of the pressurizing apparatus showing the major components of the device as well as the pressure regulator, gauge, valve and associated tubing and the hinge and latch for securing the base and the door.

As best illustrated in FIG. 2, base assembly 26 has an inner housing 28 and an outer housing 30. A hang tab 32 is formed on inner housing 28 for hanging patient fluid bag 14. Hang tab 32 comprises a U-shaped raised channel extending perpendicularly from inner housing 28 of base 26. As will be appreciated, hang tab 32 may be formed in a number of other ways without affecting the performance of pressurizing apparatus 10. As examples, a solid rectangular raised bump, a hook, or a rod configuration could also perform the function of allowing patient fluid bag 14 to be hung in a vertical position. It is also contemplated that the hang tab could be formed in or on door 24.

Door 24 and base 26 are hingedly attached to one another via a hinge 34. Hinge 34 is secured between rim 36 and ridge 38. Latch 40 fits over rim 36, on the opposite edge as hinge 34, and secures door 24 in the closed position. Latch 40 is secured to door 24 and base 26 by latch screws 42.

The pressurized fluid is conducted out of patient fluid bag 14 and through fluid tubing 44 to the medical apparatus appropriate to the application. If desired, tube clamps 46 can be used to control the flow of the fluid. Here, the fluid tubing 44 is connected via Y-connector 48 to a fluid heating assembly designated generally as 50. In other applications fluid tubing 44 would be attached to an irrigation apparatus (not shown). Further, although the presently preferred embodiment has been designed with infusion and irrigation in mind, the inventive concepts of the apparatus may also be usefully employed in other medical or industrial applications.

As best shown in FIG. 2, the base 26 comprises an inner housing 28 and an outer housing 30. Outer housing 30 is substantially rectangular in shape and is designed to provide a backing for inner housing 28 as well as a covering. Outer housing 30 has a plurality of raised cylindrical shafts 52 spaced about the periphery of outer housing 30. Each raised shaft 52 has a bore 51 therethrough for accepting housing screw 56. Bore 51 is preferably threaded although bore 51 may be unthreaded if a self tapping screw is used for housing screws 56. Housing screws 56 extend through bore 51 and into complementary raised shafts (not shown) on inner housing 28 to connect outer housing 30 and inner housing 28. If desired, other connection means, such as rivets or adhesive, may be used to secure inner housing 28 to outer housing 30. In addition, the attachment of hinge 34 and latch 40 may serve as adequate means for attaching inner housing 28 and outer housing 30.

As shown in FIG. 2, hinge 34 is a continuous hinge which is connected to inner housing 28 and outer housing 30 with hinge screws 58. Hinge screws 58 are self tapping. Rivets, adhesive or other attachment means could also be used to attach hinge 34. In the preferred embodiment hinge 34 is of metallic construction, although plastics or other materials could be employed.

Hinge 34 has a flange 60 along the distal edge. Hinge flange 60 is designed to seat in channel 62. Channel 62 is formed between rim 36, which extends around the entire periphery of door 24, and ridge 38 which extends along the distal edge of door 24. Hinge flange 60 may be secured within channel 62 with adhesive or other attachment means, such as screws 58.

Hinge 34 also has an L-shaped extension 68 which extends around the back of outer housing 30 where it is attached to outer housing 30. Formed along the side of outer housing 30 are hinge screw openings 66 to accommodate hinge screws 58. Inner housing hinge screw openings (not shown) are also formed in inner housing 28. All hinge screw openings are designed to utilize the self tapping features of hinge screws 58. L-extension openings (not shown) are formed along the back hinge edge of outer housing 30 to further secure hinge 34 to outer housing 30.

Latch 40 is similarly attached to inner housing 28 and outer housing 30. Outer housing latch screw openings 70 are formed in outer housing 30. Inner housing latch screw openings 72 are formed in inner housing 28. Latch screws 42 extend through latch 40 into outer housing 30 and inner housing 28 to secure latch 40. Latch screws 42 are preferably self tapping. Outer housing latch screw openings 70 and inner housing latch screw openings 72 are sized so as to take advantage of the self tapping features of latch screws 42. In practice, outer housing latch screw openings 70 and inner housing latch screw openings 72 serve to accurately position latch 40 onto inner housing 28 and outer housing 30.

The effect of securing hinge 34 and latch 40 in this manner to inner housing 28 and outer housing 30 is to secure inner housing 28 and outer as well. Additional means of attaching inner housing 28 and outer housing 30 may be employed but are not necessary in all applications.

FIG. 2 also shows the tubing connections between regulator 16, gauge 18, and valve 20. Pressure source tubing 22 provides input pressure to the system. Tubing 22 enters the outer housing 30 through opening 54 and attaches to regulator 16. Regulator tubing 74 connects the regulator to valve 20. Gauge tubing 76 connects gauge 18 to valve 20. A T-connector 78 is located on gauge tubing 76 and allows bladder bag tubing 80 to be connected to valve 20.

As can also be seen in FIG. 2, inner housing 28 includes a regulator opening 82, a gauge opening 84, and a valve opening 86. Although it is contemplated that these openings would be located as shown along the top portion of inner housing 28 in the preferred embodiment, clearly the location of these openings is arbitrary. Regulator opening 82 is proportioned to allow the knob portion of regulator 16 to extend therethrough. Gauge opening 84 is sized to accommodate gauge 18. Valve opening 86 is designed to allow the toggle switch of valve 20 to extend therethrough and to be so located as to allow the toggle switch to be moved into the up or "on" position and down or "off" position without encountering any interference from other portions of the device. Again, the precise placement of these openings and their associated components is arbitrary. As will be appreciated, locating regulator 16, gauge 18, and valve 20 along the bottom portion of the inner housing 28, on outer housing 30, or in other locations would not affect the operation of the present invention.

As depicted in FIG. 2, inner housing 28 also has a pendulous or squared off teardrop shaped cavity 88 formed therein. Bladder bag 90 fits into inner housing cavity 88. Preferably, bladder bag 90 is thermally formed to have substantially the same teardrop shape as inner housing cavity 88. Bladder bag 90 has a tube 92. This corresponds to opening 94 located at the top center of inner housing cavity 88 in inner housing 28. Tube 92 of bladder bag 90 passes through opening 94, connects to bladder bag tubing 80, which also connects to T-connector 78. Bladder bag 90 is inflated when the pressurizing apparatus is turned on and it is this inflation that applies pressure to patient fluid bag 14.

Door 24 also has a pendulous or squared-off teardrop shaped cavity 96 formed therein. Door cavity 96 is of a size and shape to compliment the shape of inner housing cavity 88 such that when the two are placed together a teardrop shaped pressurizing chamber is formed. This teardrop shaped pressurizing chamber is designed to be of substantially the same size and shape that a fluid bag assumes when placed in a vertical position. Due to this configuration, little or no manipulation of patient fluid bag 14 is required to close door 24.

Door 24 is preferably manufactured of clear polycarbonate although any clear material which can withstand the pressures of the pressurizing apparatus can be used. In addition, opaque plastics, metals, or other material can be utilized. If an opaque material is used, a fluid level window (not shown) or a remote fluid level indicator (not shown) could be used to monitor the patient fluid level in patient fluid bag 14.

Patient fluid bag 14 typically would contain blood, blood components, or volume expanders for an infusion application. For irrigation applications, patient fluid bag 14 would typically contain an irrigation solution. As will be appreciated, other fluids for other medical or industrial applications could also benefit from this inventive apparatus. The type of fluid contained within the patient fluid bag does not significantly effect the shape the bag assumes when placed in a vertical position. The shape of inner housing cavity 88 and door cavity 96 and the resultant pressurizing chamber shape are not, therefore, dependent on the type of fluid to be used.

Typical sizes of patient fluid bags include 250 ml, 500 ml, 1000 ml, 1500 ml, 2000 ml, and 3000 ml. For each size patient fluid bag the inner housing cavity 88 and door cavity 96 will be sized so as to substantially conform to the size and shape of a hanging fluid filled bag of each standard size. Of course, if other size bags are desired, an appropriately scaled pressurizing chamber could be formed to accommodate virtually any size patient fluid bag.

Figure 3:
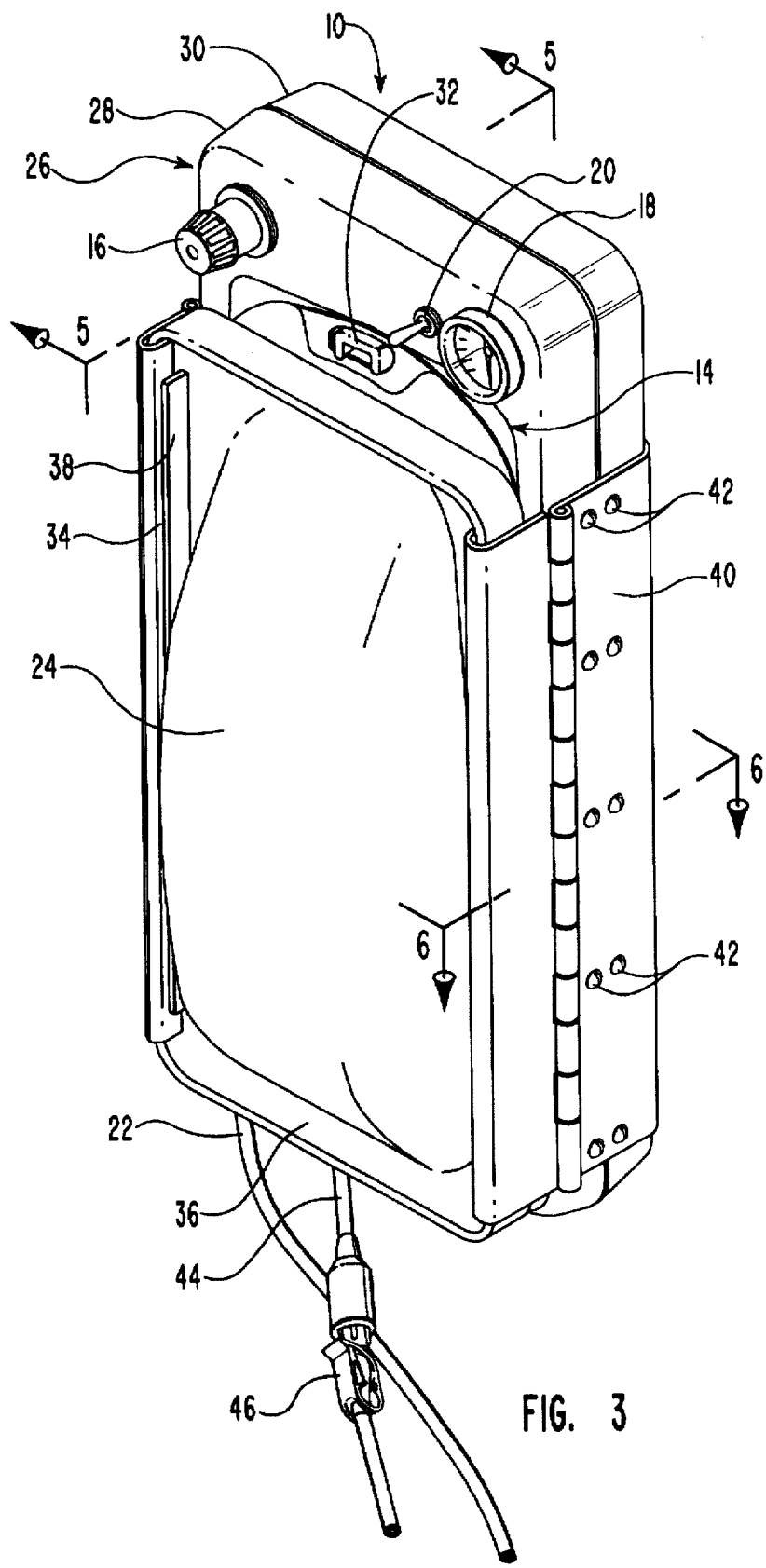
FIG. 3 is a perspective view of the assembled pressurizing apparatus.

FIG. 3 shows a perspective view of the assembled pressurizing apparatus 10. Outer housing 30 and inner housing 28 joined together to form base 26. Regulator 16, gauge 18, and valve 20 are shown in position for the preferred embodiment although, as discussed above, this positioning is not critical. Door 24 is attached to base 26 via hinge 34 and is latched in place with latch 40. Patient fluid bag 14 hangs from hang tab 32. Fluid flow through fluid tubing 44 can be controlled with tube clamp 46.

In use, door 24 is opened by depressing the latch side of the door slightly so as to allow latch 40 to be pivoted out from over the latch side of door 24. A patient fluid bag 14 is then placed on hang tab 32. Door 24 is closed over patient fluid bag 14 and latch 40 is pivoted back over door 24 so that latch 40 engages rim 36. When the bladder bag is inflated, patient fluid bag 14 presses against door 24 forcing it out slightly. Latch 40 allows door 24 to be forced out only slightly. In order to open door 24 at this stage, the bladder bag must be deflated. This allows door 24 to be depressed slightly so that latch 40 may be disengaged.

Figure 4:
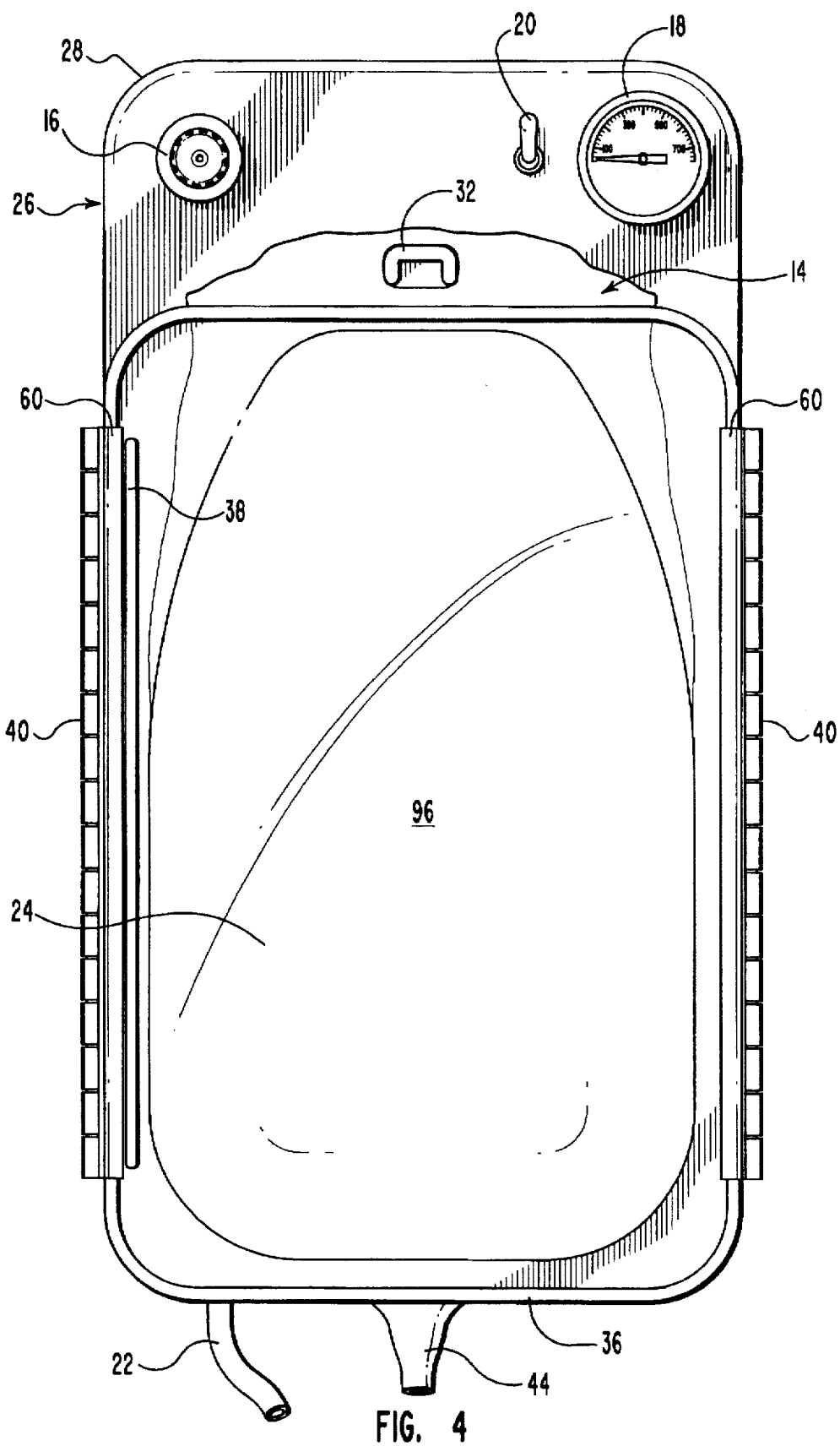
FIG. 4 is a front view of the pressurizing apparatus.

Turning to FIG. 4, which shows a front view of the assembled pressurizing apparatus 10, the general contour of door cavity 96 can best be seen. In general, door cavity 96 is rectangularly shaped in the lower quadrants and tapered in the upper quadrants. The preferred embodiment incorporates rounded corners as shown. Although door cavity 96 is depicted here as forming a raised contour in door 24, other configurations would also serve the same function. As an example, door 24 could be formed as a solid piece substantially even with rim 36. In such a configuration, channels to attach hinge 34 and latch 40 could be provided or some alternative method of attachment, such as adhesion, employed.

Figure 5A:
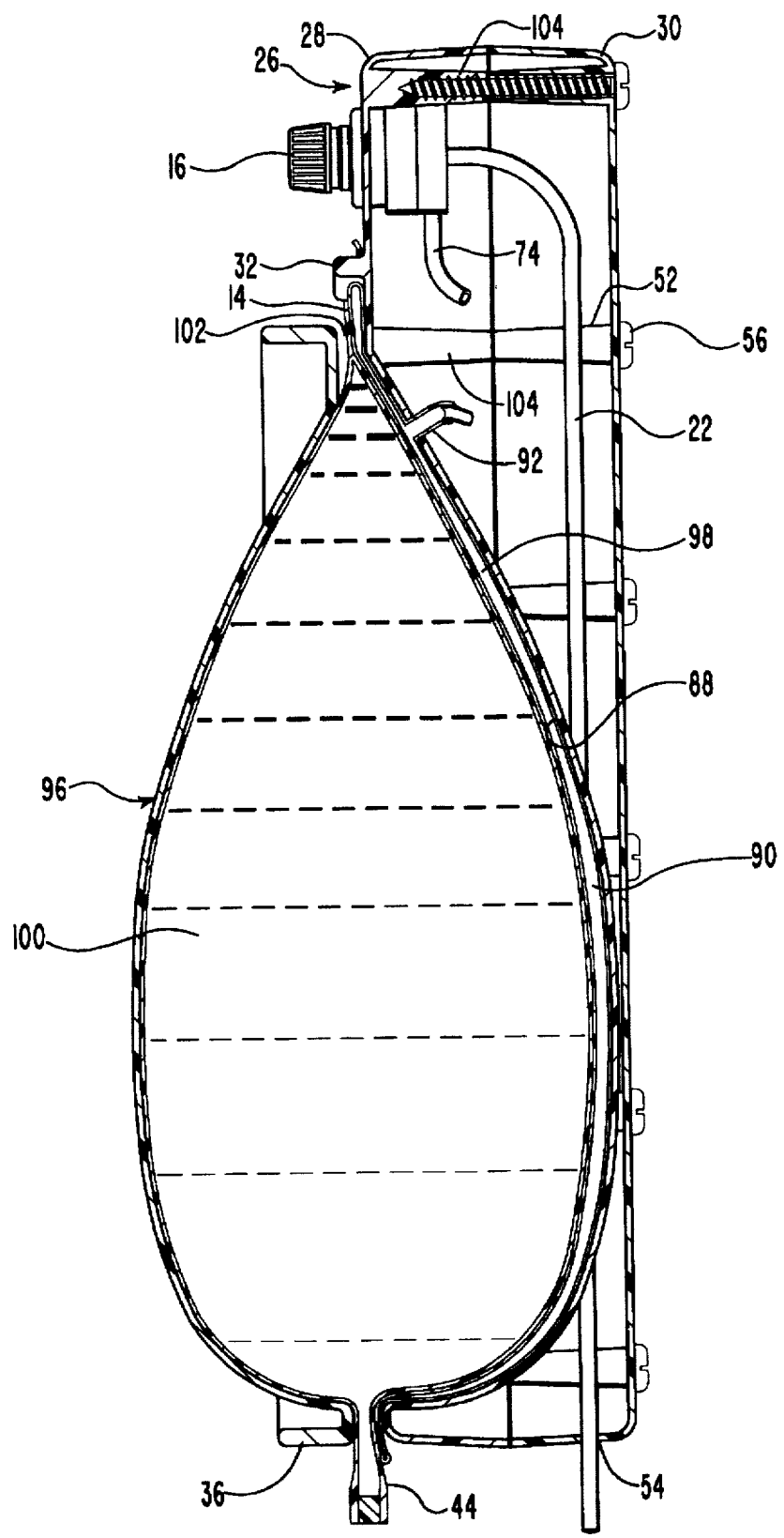
FIG. 5A is a cross section along lines 5—5 of FIG. 3 showing a substantially deflated pressurizing means.
Figure 5B:
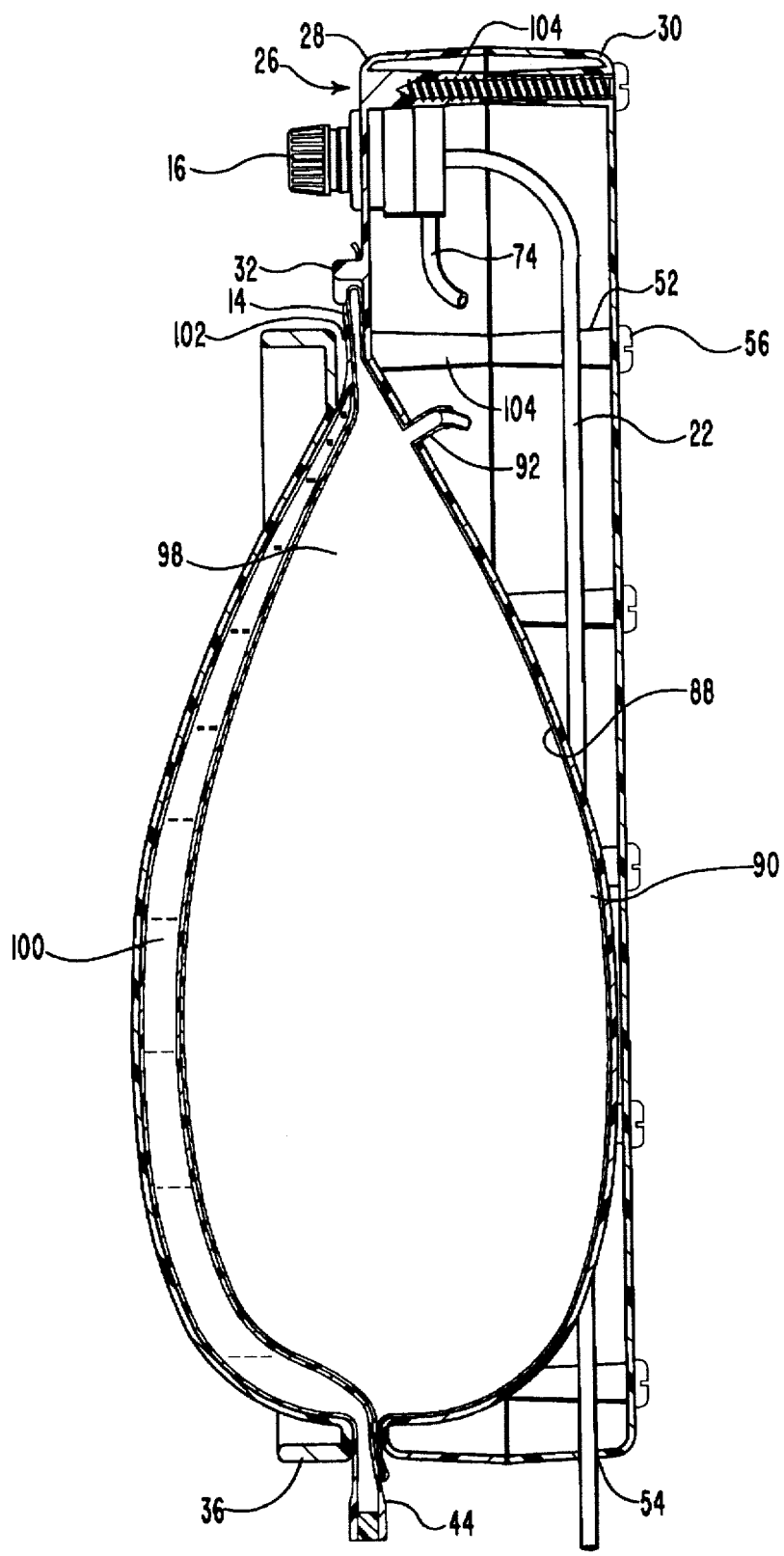
FIG. 5B is a cross section along lines 5—5 of FIG. 3 showing a substantially inflated pressurizing means.

In FIG. 5A, a cross section of the pressurizing apparatus 10, taken along lines 5—5 of FIG. 3, is shown. In this view it can be seen that fluid completely fills bag 14. In order to achieve this state, air may need to be removed from bag 14 prior to beginning a procedure.

It is particularly important that any air pocket be expunged from the system in an intravenous application since infusion of air bubbles can cause severe harm to the patient being treated. Bladder bag 90 is shown in a deflated state. The conformance of bag 14 to bladder bag 90 and door 24 result in substantially no pressure being applied to bag 14 at this stage. Pressure on bag 14 is applied only when bladder bag 90 is inflated.

Because of the conformance of the pressurizing chamber to the shape that bag 14 naturally assumes, there is no need to manipulate bag 14 to close door 24. Thus, the pressure associated with manipulating bag 14 to raise the column of fluid contained therein is not present in the inventive device.

The pressurizing chamber formed by door cavity 96 and inner housing cavity 88 conforms substantially to the shape patient fluid bag 14 assumes when hung in a vertical position, resulting in little, if any, dead space which bladder bag 90 must work against in bringing the system up to pressure. This substantially eliminates the additional, unnecessary, dead space between the top of the patient fluid bag and the contour of the door found in systems where the pressurizing chamber does not conform to the shape of the hanging patient fluid bag. In the present invention, the bladder bag is not required to work against this additional dead space in bringing the system up to pressure. The reduction in volume of the pressurizing chamber in the present invention allows the pressurizing apparatus to come up to pressure much more quickly. In addition, conforming the pressurizing chamber to the shape that patient fluid bag 14 assumes allows for easier closure of door 24 since it is no longer necessary to manipulate patient fluid bag 14 to conform to an unnatural shape. Some minor manipulation of patient fluid bag 14 may still, however, be necessary in closing door 24. The taper at the top of the teardrop conforms generally to the shape that the top of the patient fluid bag 14 takes when hung in a vertical position.

As can be seen in this view, door 24 and base 26 do not fit flush together, rather there is a gap 102 therebetween. This results from the attachment of hinge 34 and latch 40 to base 26 and door 24 so that gap 102 is formed. Variations in attachment of hinge 34 and latch 40 can be used to form gap 102 in varying widths. Preferably, gap 102 is just wide enough to allow patient fluid bag 14 to extend out on top so that it may be hung on hang tab 28 and for fluid tubing 44 to extend out on the bottom. Although gap 102 is the preferred method of accomplishing these tasks, other means can be employed. By way of example, door 24 and base 26 could be mounted flush together and an opening formed in either the door or the base or both to allow for the necessary protrusion of patient fluid bag 14.

As further shown in FIG. 5A, in one presently preferred embodiment, the contours of housing cavity 88 and door cavity 96 are asymmetrical, with door cavity 96 being somewhat flatter than housing cavity 88, such that the center line of the pressure chamber approximately coincides with the front plane of inner housing 28. Further, the dimensions and shape of housing cavity 88, door cavity 96 and bladder bag 90 are configured such that, when bladder bag 90 is completely inflated, bladder bag 90 completely fills the pressure chamber formed by housing cavity 88 and door cavity 96 without stretching or distending the walls of bladder bag 90. In this manner, when bladder bag 90 is fully inflated, bladder bag 90 completely fills the pressure chamber without stretching bladder bag 90.

FIG. 5A also illustrates that the outer periphery bladder bag 90 extends slightly beyond the periphery of the pressure chamber. In one presently preferred embodiment, the outer periphery of bladder bag 90 extends approximately one-half inch beyond the periphery of the pressured chamber.

FIG. 5B is, again, a cross section of pressurizing apparatus 10 along lines 5—5 of FIG. 3. Here, bladder bag 90 is substantially inflated and the approximate conformance between door 24 and bladder bag 90 can be viewed. This conformance results in substantially even application of pressure to bag 14. Thus, the pressure reading on gauge 18 will be an accurate representation of the pressure of fluid leaving bag 14. A related result is uniform pressure throughout the procedure.

Figure 6:
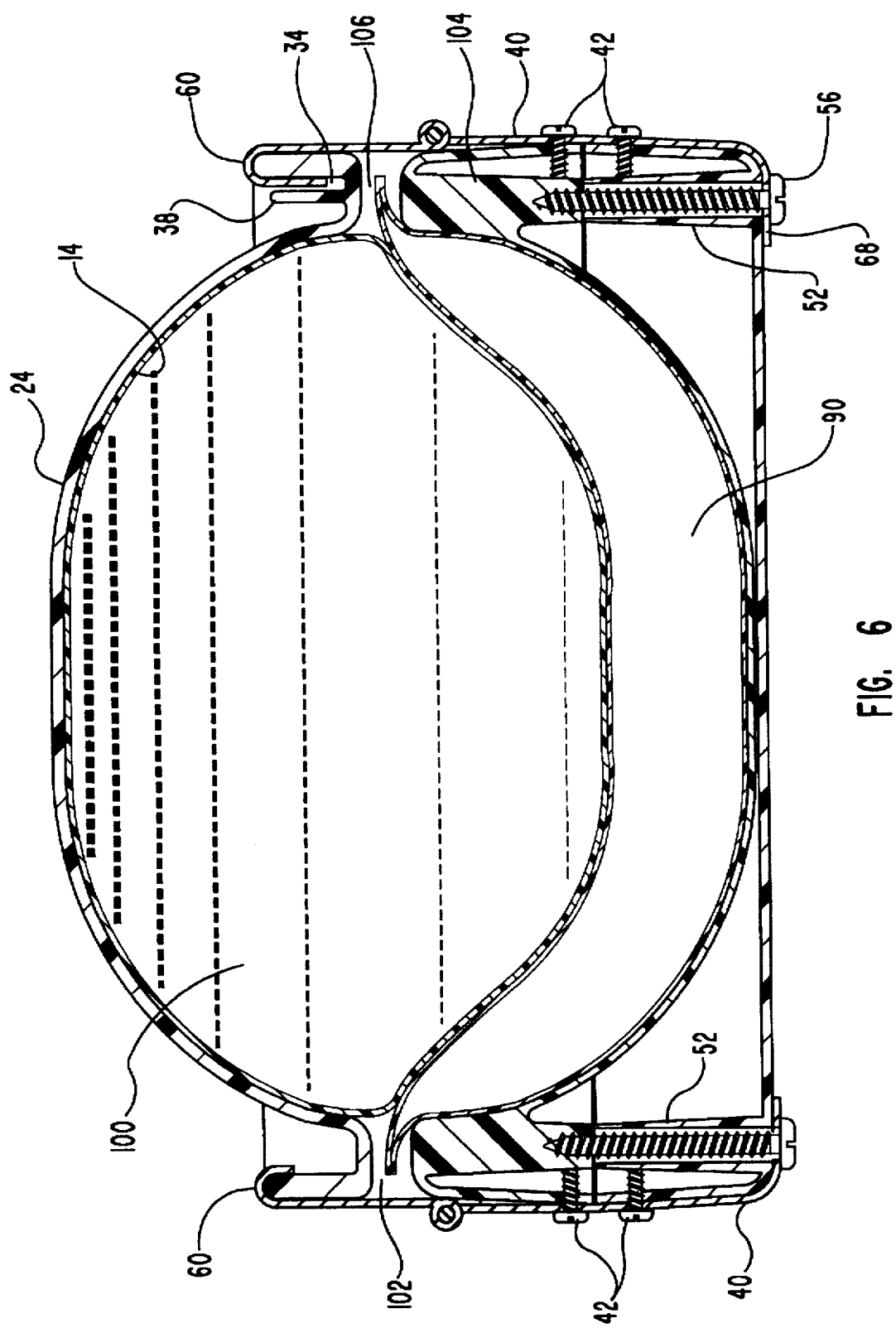
FIG. 6 is a cross section along lines 6—6 of FIG. 3.

FIG. 6 depicts a cross section of the present invention along lines 6—6 of FIG. 3 with bladder bag 90 partially inflated. The conformities between inner cavity 88, bladder bag 90, patient fluid bag 14, and door cavity 96 are readily apparent from this view. Such conformity is present throughout the pressurizing chamber of the present invention.

Patient fluid bag 14 assumes a generally rectangular shape of substantially consistent cross section when lying horizontally on a flat surface. When a patient fluid bag is hung in a vertical position, the fluid inside the bag naturally assumes a teardrop shape. The force of gravity pulls the fluid toward the bottom of the bag as much as the bag itself will allow. The pressurizing chamber of the present invention substantially mimics this teardrop shape. Door 24 and base 26 split the teardrop substantially in half along a vertical axis. By mimicking the shape which a filled patient fluid bag naturally assumes, the user is able to easily close door 24 since the chamber is large at the bottom, as is the patient fluid bag, and tapers off at the top, as does the patient fluid bag. At the same time the overall volume of the pressurizing chamber is reduced. Reducing the volume of the pressurizing chamber results in less time to bring the pressurizing apparatus 10 up to the preset pressure. There is less initial volume which the pressure source must overcome. In other words, bladder bag 90 need not be inflated as much to achieve the same effect since there is less space to fill.

Also best seen in this view are inner housing attachment posts 104. Inner housing attachment posts 104 engage housing screws 56 when housing screws 56 are inserted through shafts 52. In the preferred embodiment inner housing attachment posts 104 have a threaded bore (not shown) therethrough.

The present invention may be embodied in other specific forms without departing from its essential characteristics. The described embodiments are to be considered in all respects only as illustrative and not restrictive. The scope of the invention is, therefore, indicated by the appended claims rather than by the foregoing description.

What is claimed is:

1. A patient fluid bag pressurizing apparatus comprising:

a base having a teardrop shaped cavity formed therein;

a door having a complimentary teardrop shaped cavity formed therein;

attachment means for openingly attaching the base and the door thereby forming a teardrop shaped pressurizing chamber when the door is in a closed position;

a hook for hanging a patient fluid bag within the teardrop shaped pressurizing chamber; and pressuring means for applying pressure to the patient fluid bag when the patient fluid bag is hanging within the teardrop shaped pressurizing chamber with the door closed.

2. A patient fluid bag pressurizing apparatus as defined in claim 1 wherein said door is constructed of a transparent plastic material.

3. A patient fluid bag pressurizing apparatus as defined in claim 1 wherein the teardrop shaped pressurizing chamber is constructed of high impact plastic materials capable of withstanding the application of high pressure.

4. A patient fluid bag pressurizing apparatus as defined in claim 1 wherein the pressurizing means comprises a bladder bag positioned within the teardrop shaped cavity formed in the base and constructed to substantially conform to the teardrop shape of the base when deflated, and further to substantially conform to the teardrop shape of the pressurizing chamber when the bladder bag is inflated.

5. A patient fluid bag pressurizing apparatus as defined in claim 1 wherein said door is constructed of a transparent plastic material.

6. A patient fluid bag pressurizing apparatus as defined in claim 1 wherein the teardrop shaped pressurizing chamber is constructed of high impact plastic materials capable of withstanding the application of high pressure.

7. A patient fluid bag pressurizing apparatus comprising:

a base having a teardrop shaped cavity formed therein;

a door having a complimentary teardrop shaped cavity formed therein;

attachment means for openingly attaching the base and the door thereby forming a teardrop shaped pressurizing chamber when the door is in a closed position;

a hook for hanging a patient fluid bag within the teardrop shaped pressurizing chamber; and pressurizing means for applying pressure to the patient fluid bag when the patient fluid bag is hanging within the teardrop shaped pressurizing chamber with the door closed, a bladder bag, the bladder bag positioned within the teardrop shaped cavity formed in the base, wherein the bladder bag is constructed to substantially conform to the teardrop shape of the base when deflated, and further to substantially conform to the teardrop shape of the pressurizing chamber when the bladder bag is inflated, wherein the bladder bag is connected to a valve to allow inflation and deflation the bladder bag, the pressurizing means further comprising a gauge for monitoring the pressure and a regulator for adjusting the pressure.

8. A patient fluid bag pressurizing apparatus as defined in claim 7 wherein said door in constructed of a transparent plastic material.

9. A patient fluid bag pressurizing apparatus as defined in claim 7 wherein the teardrop shaped pressurizing chamber is constructed of plastic materials capable of withstanding the application of high pressure.

10. A patient fluid bag apparatus as defined in claim 7 wherein bladder bag is thermally formed in a teardrop shape to conform to the contour of the teardrop shaped cavity formed in the base.

11. A patient fluid bag pressurizing apparatus comprising:

a base having a teardrop shaped cavity formed therein;

a door having a complimentary teardrop shaped cavity formed therein;

a continuous hinge openingly connecting the base and the door thereby forming a teardrop shaped pressurizing chamber when the door is in a closed position;

latch means for holding the door in a closed position;

a hook for hanging a patient fluid bag within the teardrop shaped pressurizing chamber; and pressurizing means for applying pressure to the patient fluid bag when the patient fluid bag is hanging within the teardrop shaped pressurizing chamber with the door closed, comprising a teardrop shaped bladder bag, the bladder bag conforming to and positioned within the teardrop shaped cavity formed in the base, wherein the bladder bag is connected to a valve to allow inflation and deflation of the bladder bag, the pressurizing means further comprising a gauge for monitoring the pressure and a regulator for adjusting the pressure.

12. A patient fluid bag pressurizing apparatus as defined in claim 11 wherein said door in constructed of a transparent plastic material.

13. A patient fluid bag pressurizing apparatus as defined in claim 11 wherein the teardrop shaped pressurizing chamber is constructed of high impact plastic materials capable of withstanding the application of high pressure.

14. A patient fluid bag pressurizing apparatus as defined in claim 11 wherein the bladder bag is thermally formed in a teardrop shape to conform to the contour of the teardrop shaped cavity formed in the base.

15. A patient fluid bag pressurizing apparatus as defined in claim 11 wherein the continuous hinge in constructed of metal.

16. A patient fluid bag pressurizing apparatus as defined in claim 11 wherein the continuous hinge and latch means are constructed of a plastic material.

17. A patient fluid bag pressurizing apparatus as defined in claim 11 wherein said door portion is constructed of a transparent material.

18. A patient fluid bag pressurizing apparatus as defined in claim 11 wherein said door portion is constructed of an opaque material and further comprises a transparent window located on said door portion whereby the fluid level can be viewed.

* * * * *